US005705094A

United States Patent [19]
Takeuchi et al.

[11] Patent Number: 5,705,094
[45] Date of Patent: Jan. 6, 1998

[54] ANTIFERROELECTRIC LIQUID CRYSTAL COMPOSITION AND LIQUID CRYSTAL DISPLAY ELEMENT USING THE SAME

[75] Inventors: Akira Takeuchi, Nishio; Norio Yamamoto, Kariya; Takayuki Fujikawa; Toshio Yamamoto, both of Nishio, all of Japan

[73] Assignee: Nippon Soken, Inc., Aichi, Japan

[21] Appl. No.: 503,970

[22] Filed: Jul. 19, 1995

[30] Foreign Application Priority Data

Jul. 19, 1994 [JP] Japan .................. 6-166872
Mar. 23, 1995 [JP] Japan .................. 7-64154

[51] Int. Cl.$^6$ .......... C09K 19/52; C09K 19/12; C09K 19/30; C09K 19/34
[52] U.S. Cl. .............. 252/299.01; 252/299.63; 252/299.65; 252/299.66; 252/299.67; 252/299.61; 252/299.62
[58] Field of Search .......... 252/299.66, 299.67, 252/299.01, 299.65, 299.61, 299.62, 299.63

[56] References Cited

U.S. PATENT DOCUMENTS

| | | | |
|---|---|---|---|
| 4,576,732 | 3/1986 | Isogai | 252/299.65 |
| 4,754,051 | 6/1988 | Sasaki | 560/8 |
| 4,921,632 | 5/1990 | Nakamura et al. | 252/299.1 |
| 4,961,874 | 10/1990 | Takeuchi | 252/299.6 |
| 5,046,823 | 9/1991 | Mori et al. | 359/56 |
| 5,110,498 | 5/1992 | Suzuki et al. | 252/299.66 |
| 5,151,213 | 9/1992 | Reiffenrath | 252/299.6 |
| 5,171,471 | 12/1992 | Suzuki et al. | 252/299.61 |
| 5,184,847 | 2/1993 | Suzuki et al. | 252/299.65 |
| 5,204,020 | 4/1993 | Suzuki | 252/299.67 |
| 5,262,086 | 11/1993 | Suzuki et al. | 252/299.65 |
| 5,316,694 | 5/1994 | Murashiro | 252/299.61 |
| 5,330,678 | 7/1994 | Okabe et al. | 252/299.62 |
| 5,344,586 | 9/1994 | Suzuki et al. | 252/299.64 |
| 5,352,382 | 10/1994 | Johno | 252/299.65 |
| 5,356,562 | 10/1994 | Greenfield | 252/299.63 |
| 5,374,375 | 12/1994 | Yui | 252/299.65 |
| 5,378,392 | 1/1995 | Murashiro | 252/299.01 |
| 5,378,396 | 1/1995 | Yui | 252/299.65 |
| 5,393,460 | 2/1995 | Okabe | 252/299.65 |
| 5,417,885 | 5/1995 | Suzuki | 252/299.65 |

FOREIGN PATENT DOCUMENTS

| | | |
|---|---|---|
| 330491 | 8/1989 | European Pat. Off. . |
| 339987 | 11/1989 | European Pat. Off. . |
| 0517504A1 | 12/1992 | European Pat. Off. . |
| 0525737A1 | 2/1993 | European Pat. Off. . |
| 0562627A1 | 9/1993 | European Pat. Off. . |
| 0582519A1 | 2/1994 | European Pat. Off. . |
| 582 468 | 2/1994 | European Pat. Off. . |
| 1-139551 | 6/1989 | Japan . |
| 1213390 | 8/1989 | Japan . |
| 1316339 | 12/1989 | Japan . |
| 1316367 | 12/1989 | Japan . |
| 228128 | 1/1990 | Japan . |
| 2-69440 | 3/1990 | Japan . |

OTHER PUBLICATIONS

Nishiyama et al., "Effect of Size of the Lateral Substituent at the Chiral Centre on the Stability of Some Chiral Smectic Liquid–crystalline Phases" Journal of Materials Chemistry 3 (1993) No. 2, Cambridge, GB, pp. 149–159.

Suzuki et al., "New Fluorine–Containing Ferroelectric Liquid Crystal Compounds Showing Tristable Switching" Liquid Crystals, 1989, vol. 6, No. 2, London, pp. 167–174.

Database WPI/Derwent Publications Ltd., London, GB, Sep. 1994 re JP–A–06–271,852.

Chandani, et al: "Tristable Switching in Surface Ferroelectric Liquid Crystals with a Large Spontaneous Polarization", Japanese Journal of Applied Physics, vol. 27, No. 5,May 1988,pp.L729–L732.

Meyer: "Ferroelectric Liquid Crystals; a Review", Mol. Cryst.Liq.Cryst., 1977, vol. 40, pp. 33–48.

*Primary Examiner*—C. H. Kelly
*Attorney, Agent, or Firm*—Cushman, Darby & Cushman IP Group of Pillsbury Madison & Sutro LLP

[57] ABSTRACT

The antiferroelectric liquid crystal composition comprising at least one chiralsmectic liquid crystal compound having a positive specific rotatory power $[\alpha]_D^{25}$ and at least one chiralsmectic liquid crystal compound having a negative specific rotatory power, and the value of the specific rotatory power of the composition is between −25° and +25° C. This invention provides a method for blending liquid crystal compounds to form an antiferroelectric liquid crystal composition which has a decreased dark luminance of a liquid crystal display element.

14 Claims, 6 Drawing Sheets

ANTIFERROELECTRIC LIQUID CRYSTAL COMPOSITION AND LIQUID CRYSTAL DISPLAY ELEMENT USING THE SAME

BACKGROUND OF THE INVENTION

1. Field of the Invention

This invention relates to a liquid crystal composition. Particularly this invention relates to a liquid crystal composition having an ability to indicate an antiferroelectric phase (chiralsmectic $C_A$ phase, hereinafter abbreviated to "SmC$_A$* phase"). More particularly, this invention relates to an antiferroelectric liquid crystal composition suitable for use in a liquid crystal display element.

2. Description of the Related Art

Recently, liquid crystal displays have become widely used as display elements, due to their thin thickness, light weight, low electricity consumption etc. However, most of these displays use TN (Twisted Nematic) type displays comprising a nematic liquid crystal. Since the driving of the displays of the TN type is based on the anisotropy of the dielectric constant of the liquid crystal, the speed of response is slow, and an improvement is required.

In contrast, liquid crystal devices comprising chiralsmectic C phase (hereinafter abbreviated as "SmC* phase") liquid crystals, which are ferroelectric and were discovered by Meyer et. al., have a high speed response and memory characteristics which are not attained by nematic liquid crystals. Thus, the application of ferroelectric liquid crystals to a ferroelectric liquid crystal display is being vigorously researched. However, the good orientation and memory characteristics required for this indication method are difficult to realize in a real display. For example, the display has the problems that it is not resistant to external shocks etc., and many problems must be solved.

On the other hand, recently, an antiferroelectric phase (hereinafter abbreviated as "SmC$_A$* phase") has been discovered which shows three stable states on the lower temperature side of said SmC* phase, by Chandani et. al. This antiferroelectric liquid crystal shows a thermodynamically stable phase wherein dipoles are arranged in antiparallel in every adjacent layer, and exhibits an electric field-induced phase transition between the antiferroelectric phase and the ferroelectric phase, which is characterized by a clear threshold value and double hysteresis characteristics in response to an applied voltage. Research on a new displaying method utilizing this switching behavior, for example, an antiferroelectric liquid crystal display etc., has already begun.

Figure 1:
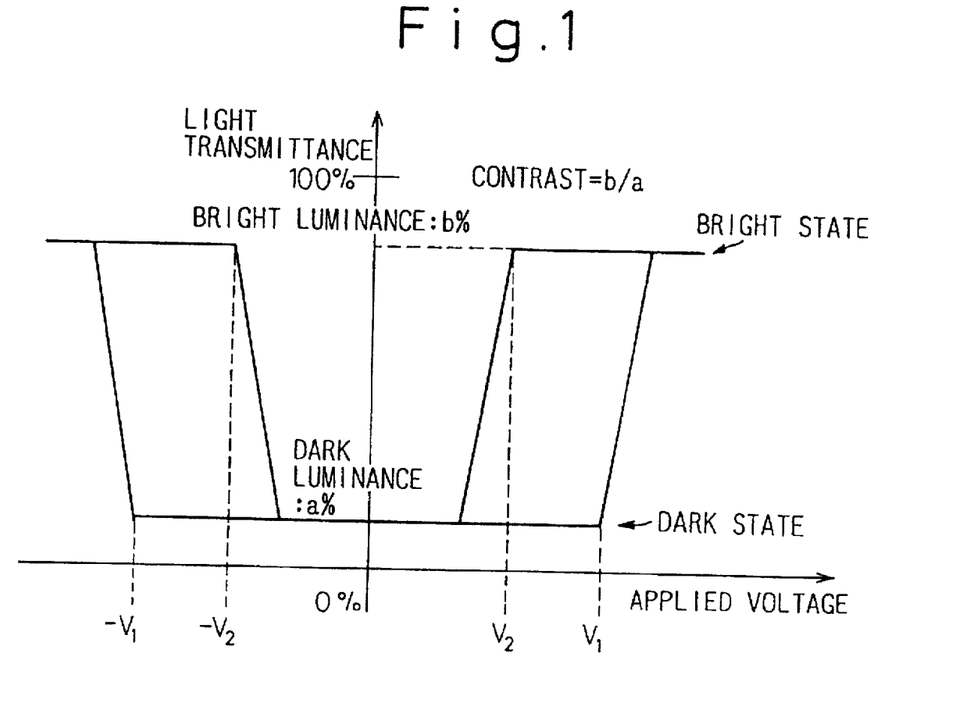
FIG. 1 is a graph schematically showing applied voltage and light transmittance of an antiferroelectric liquid crystal element using an antiferroelectric liquid crystal having the $SmC_A^*$ phase.

The relation between applied voltage and transmitted light intensity in the antiferroelectric liquid crystal element using an antiferroelectric liquid crystal having SmC$_A$* phase shows a double hysteresis characteristics as shown in FIG. 1. This figure is obtained by placing in a polarization microscope having a photomultiplier an antiferroelectric liquid crystal display element made by injecting antiferroelectric material into a cell obtained by sticking two glass substrates together, the surfaces of which have been orientation treated, putting a spacer between the substrates, applying a chopping wave to the element under a crossed Nicols, and measuring the variation in transmitted light. In the display element, the response from a dark luminance to a bright luminance utilizing the double hysteresis characteristics is attained at the time of exceeding a threshold value $V_1$ in the course of increasing the applied voltage, and the response from the bright state to the dark state is attained at the time of dropping behind a threshold voltage $V_2$ in the course of decreasing the applied voltage.

The contrast of the antiferroelectric liquid crystal display element can be expressed by a rate of (bright luminance)/(dark luminance), where the bright luminance corresponds to b% in FIG. 1, and dark luminance corresponds to a% in FIG. 1. These values can be obtained by setting the luminance, when the polarizing microscope light source is adjusted to always exhibit a fixed light transmittance amount, as 100%, and the luminance in a completely shielded state as 0%.

In order to increase the contrast, decreasing of the dark luminance can be said to be effective from the above definition of the contrast. The dark luminance is the light transmittance when no electric field is applied, and depends on the extent of the orientation of the liquid crystal compound or liquid crystal mixed composition used in the display element. Usually, in order to obtain practical physical properties, several antiferroelectric liquid crystal compounds and compounds having no antiferroelectric property are mixed and used. However, in accordance with the constitutional proportion, the orientation state thereof is often bad, which increases the leakage of light, and the dark luminance. However, heretofore, there has been no blend guideline to improve the orientation state of the antiferroelectric liquid crystal composition and decrease the dark luminance.

The present inventors have studied the relation between several liquid crystal properties (helical pitch and layer gap etc.) and the dark luminance for several hundred chiralsmectic liquid crystals including antiferroelectric liquid crystals and several hundred liquid crystal compositions. As the result, they found qualitatively that the longer the helical pitch of compositions is, and the wider the layer gap is, the larger the decrease in dark luminance. However, they could not find a quantitative relation between the properties of the composition and the dark luminance.

SUMMARY OF THE INVENTION

An object of the present invention is to provide a method for determining the composition of a blend of an antiferroelectric liquid crystal composition for decreasing the dark luminance of a liquid crystal display element, and an antiferroelectric liquid crystal element having a high contrast.

The present inventors have studied diligently the relations between the physical properties of liquid crystals and the dark luminance and have found that when the specific rotatory power of an antiferroelectric liquid crystal composition is in a specific range, which composition comprises at least one chiralsmectic liquid crystal compound having a positive specific rotatory power and at least one chiralsmectic liquid crystal compound having a negative specific rotatory power, or when the weight ratio of said two kinds of compounds is in a specific range, the dark luminance of a display device using the composition effectively decreases, and attained the present invention.

Figure 2:
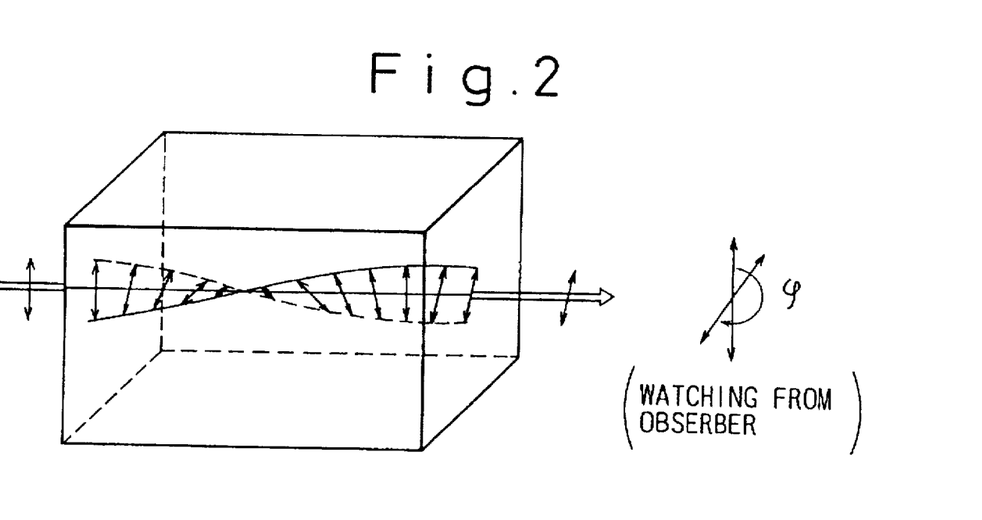
FIG. 2 shows the linear polarization of light being rotated as it passes through an optically active substance.

Here, the specific rotatory power will be described. When light with linear polarization passes through an isotropic material, the direction of the polarization does not change. However, some materials have the property of rotating the plane of polarization of light passing through these materials (FIG. 2). For example, the sucrose solution is typical and famous. This phenomenon was discovered in the 1810s, and is called as optical rotating power or optical activity.

The rotated angle φ is proportional to the concentration c of the optically active solution and the distance L in which the light has passed. When a solution of 100 cm$^3$ contains c grams of solute, and L is represented by the unit dm (10 cm), the specific rotatory angle [α] in degrees, is calculated by the following formula:

$$[\alpha] = 100 \, \phi/Lc \text{ (degrees)}$$

In this invention, in every case, the values of specific rotatory power were determined at 25° C., with a solution obtained by dissolving a liquid crystal or a liquid crystal composition in a chloroform solution, using the sodium lamp D-line wavelength (about 586 nm).

The first feature of the present invention is an antiferroelectric liquid crystal composition comprising a chiralsmectic liquid crystal compound having a positive specific rotatory power $[\alpha]_D^{25}$ (hereinafter the specific rotatory powers described are $[\alpha]_D^{25}$) and a chiralsmectic liquid crystal compound having a negative specific rotatory power, and the value of the specific rotatory power of the composition is between −25° and +25°.

The second feature of the present invention is an antiferroelectric liquid crystal composition according to the first feature wherein the chiralsmectic liquid crystal compounds have an asymmetric chemical constitution represented by the following formula (I).

wherein, R is any one of $CH_3$, $CF_3$, $C_2H_5$ and $C_2F_5$.

The third feature of the present invention is an antiferroelectric liquid crystal composition according to the first feature wherein the chiralsmectic liquid crystal compounds are an optically active compound represented by the following general formula, wherein, m is an integer of 1 to 18; n is an integer of 3 to 10; A, B and C is one or combination of two selected from the following formulae (III); $X^1$, $X^2$ and $X^3$ are independently selected from the following formulae (IV); $Z^1$, $Z^2$ and $Z^3$ are independently selected from the following formulae (V); Y is any of $CH_3$, $CF_3$, $C_2H_5$ and $C_2F_5$.

(III):

(IV): single bond (—), —COO—, —OCO—, —CO—, —O—, —$CH_2$O— and —C≡C—.

(V): H, F, Cl, Br, CN and $CH_3$.

The fourth feature of the present invention is an antiferroelectric liquid crystal composition comprising a chiralsmectic liquid crystal compound represented by the formula (II) wherein the absolute configuration is R type and the specific rotatory power has a positive value (wherein Y is preferably $CF_3$), and a chiralsmectic liquid crystal compound represented by the formula (II) wherein the absolute configuration is R type and the specific rotatory power has a negative value (wherein Y is preferably $CH_3$), the composition has a specific rotatory power of from 0° to +25°.

The fifth feature of the present invention is an antiferroelectric liquid crystal composition comprising a chiralsmectic liquid crystal compound represented by the formula (II) wherein the absolute configuration is S type and the specific rotatory power has a negative value (wherein Y is preferably $CF_3$), and a chiralsmectic liquid crystal compound represented by the formula (II) wherein the absolute configuration is S type and the specific rotatory power has a positive value (wherein Y is preferably $CH_3$), the composition has a specific rotatory power of from −25° to 0°.

The 6th feature of the present invention is an antiferroelectric liquid crystal composition comprising a chiralsmectic liquid crystal compound represented by the formula (II) wherein the absolute configuration is R type and the specific rotatory power has a positive value (wherein Y is preferably $CF_3$), and a chiralsmectic liquid crystal compound represented by the formula (II) wherein the absolute configuration is S type and the specific rotatory power has a negative value (wherein Y is preferably $CF_3$), the composition has a specific rotatory power of from −25° to +25°.

The 7th feature of the present invention is an antiferroelectric liquid crystal composition comprising a chiralsmectic liquid crystal compound represented by the formula (II) wherein the absolute configuration is R type and the specific rotatory power has a negative value (wherein Y is preferably $CH_3$), and a chiralsmectic liquid crystal compound represented by the formula (II) wherein the absolute configuration is S type and the specific rotatory power has a positive value (wherein Y is preferably $CH_3$), the composition has a specific rotatory power of from −25° to +25°.

The 8th feature of the present invention is an antiferroelectric liquid crystal composition comprising 40 to 90% by weight of a chiralsmectic liquid crystal compound represented by the formula (II) wherein the absolute configuration is R type and the specific rotatory power has a positive value, and 10 to 60% by weight of a chiralsmectic liquid crystal compound represented by the formula (II) wherein the absolute configuration is R type and the specific rotatory power has a negative value.

The 9th feature of the present invention is an antiferroelectric liquid crystal composition comprising 40 to 90% by weight of a chiralsmectic liquid crystal compound represented by the formula (II) wherein the absolute configuration is S type and the specific rotatory power has a negative value, and 10 to 60% by weight of a chiralsmectic liquid crystal compound represented by the formula (II) wherein the absolute configuration is S type and the specific rotatory power has a positive value.

The 10th feature of the present invention is an antiferroelectric liquid crystal composition comprising 20 to 80% by weight of a chiralsmectic liquid crystal compound represented by the formula (II) wherein the absolute configuration is R type and the specific rotatory power has a positive value, and 20 to 80% by weight of a chiralsmectic liquid crystal compound represented by the formula (II) wherein the absolute configuration is S type and the specific rotatory power has a negative value.

The 11th feature of the present invention is an antiferroelectric liquid crystal composition comprising 20 to 80% by weight of a chiralsmectic liquid crystal compound represented by the formula (II) wherein the absolute configuration is R type and the specific rotatory power has a negative value, and 20 to 80% by weight of a chiralsmectic liquid crystal compound represented by the formula (II) wherein the absolute configuration is S type and the specific rotatory power has a positive value.

The 12th feature of the present invention is a liquid crystal display device using any of the liquid crystal compositions of the features 1 to 11.

The present inventors have determined the specific rotatory powers of many disclosed chiralsmectic liquid crystal compounds. Examples of the chiralsmectic compounds mixed into the antiferroelectric liquid crystal composition of the present inventions are as follows.

(a) Compounds having a positive specific rotatory power:
R enantiomers of the absolute configuration of the following compounds (1) to (20) and S enantiomers of the absolute configuration of the following compounds (21) to (31); and (b) Compounds having a negative specific rotatory power:
R enantiomers of the absolute configuration of the following compounds (21) to (31) and S enantiomers of the absolute configuration of the following compounds (1) to (20).

Compound (1)

$(R)-C_mH_{2m+1}O-$⟨ring⟩$-$⟨ring⟩$-COO-$⟨ring⟩$-COOCH(CF_3)C_nH_{2n+1}$

| Compound No. | m | n | Specific Rotatory Power | Compound No. | m | n | Specific Rotatory Power |
|---|---|---|---|---|---|---|---|
| (1)-1 | 8 | 6 | +32.4 | (1)-7 | 10 | 6 | +31.1 |
| (1)-2 | 8 | 8 | +33.2 | (1)-8 | 10 | 8 | +30.8 |
| (1)-3 | 9 | 4 | +29.1 | (1)-9 | 11 | 6 | +28.6 |
| (1)-4 | 9 | 5 | +30.5 | (1)-10 | 11 | 8 | +30.5 |
| (1)-5 | 9 | 8 | +32.0 | (1)-11 | 12 | 6 | +29.4 |
| (1)-6 | 10 | 4 | +29.1 | (1)-12 | 12 | 8 | +31.9 |

Compound (2)

$(R)-C_mH_{2m+1}-$⟨ring⟩$-$⟨ring⟩$-COO-$⟨ring⟩$-COOCH(CF_3)C_nH_{2n+1}$

| Compound No. | m | n | Specific Rotatory Power | Compound No. | m | n | Specific Rotatory Power |
|---|---|---|---|---|---|---|---|
| (2)-1 | 8 | 6 | +32.4 | (2)-6 | 10 | 4 | +28.9 |

-continued

| | | | | | | | |
|---|---|---|---|---|---|---|---|
| (2)-2 | 8 | 8 | +32.7 | (2)-7 | 10 | 6 | +30.1 |
| (2)-3 | 9 | 4 | +29.4 | (2)-8 | 10 | 8 | +31.0 |
| (2)-4 | 9 | 5 | +32.2 | (2)-9 | 11 | 6 | +30.1 |
| (2)-5 | 9 | 8 | +33.1 | (2)-10 | 11 | 8 | +31.1 |

Compound (3)

| Compound No. | m | n | Specific Rotatory Power | Compound No. | m | n | Specific Rotatory Power |
|---|---|---|---|---|---|---|---|
| (3)-1 | 8 | 6 | +31.2 | (3)-6 | 10 | 4 | +27.1 |
| (3)-2 | 8 | 8 | +32.0 | (3)-7 | 10 | 6 | +28.8 |
| (3)-3 | 9 | 4 | +28.0 | (3)-8 | 10 | 8 | +29.9 |
| (3)-4 | 9 | 5 | +30.2 | (3)-9 | 11 | 8 | +29.5 |
| (3)-5 | 9 | 8 | +32.1 | (3)-10 | 12 | 8 | +28.7 |

Compound (4)

| Compound No. | m | n | Specific Rotatory Power |
|---|---|---|---|
| (4)-1 | 8 | 8 | +29.0 |
| (4)-2 | 9 | 5 | +28.5 |
| (4)-3 | 10 | 4 | +26.0 |

Compound (5)

| Compound No. | m | n | Specific Rotatory Power | Compound No. | m | n | Specific Rotatory Power |
|---|---|---|---|---|---|---|---|
| (5)-1 | 9 | 4 | +27.0 | (5)-4 | 10 | 4 | +25.8 |
| (5)-2 | 9 | 5 | +29.0 | (5)-5 | 10 | 8 | +28.2 |
| (5)-3 | 9 | 8 | +28.8 | | | | |

Compound (6)

| Compound No. | m | n | Specific Rotatory Power |
|---|---|---|---|
| (6)-1 | 8 | 6 | +30.7 |
| (6)-2 | 9 | 6 | +29.3 |

Compound (7)

| Compound No. | m | n | Specific Rotatory Power |
|---|---|---|---|
| (7)-1 | 9 | 6 | +26.5 |
| (7)-2 | 9 | 8 | +26.8 |

-continued

Compound (8)

| Compound No. | m | n | Specific Rotatory Power | Compound No. | m | n | Specific Rotatory Power |
|---|---|---|---|---|---|---|---|
| (8)-1 | 8 | 6 | +32.8 | (8)-5 | 10 | 8 | +30.5 |
| (8)-2 | 9 | 6 | +32.7 | (8)-6 | 11 | 6 | +30.4 |
| (8)-3 | 9 | 8 | +30.7 | (8)-7 | 11 | 8 | +29.8 |
| (8)-4 | 10 | 6 | +31.6 | (8)-8 | 12 | 6 | +30.3 |

Compound (9)

| Compound No. | m | n | Specific Rotatory Power |
|---|---|---|---|
| (9)-1 | 8 | 6 | +29.8 |

Compound (10)

| Compound No. | m | n | Specific Rotatory Power | Compound No. | m | n | Specific Rotatory Power |
|---|---|---|---|---|---|---|---|
| (10)-1 | 9 | 6 | +28.2 | (10)-4 | 10 | 8 | +27.2 |
| (10)-2 | 9 | 8 | +27.3 | (10)-5 | 11 | 6 | +27.4 |
| (10)-3 | 10 | 6 | +27.5 | (10)-6 | 11 | 8 | +26.2 |

Compound (11)

| Compound No. | m | n | Specific Rotatory Power |
|---|---|---|---|
| (11)-1 | 9 | 6 | +30.2 |
| (11)-2 | 10 | 6 | +29.4 |
| (11)-3 | 10 | 8 | +28.8 |

Compound (12)

| Compound No. | m | n | Specific Rotatory Power | Compound No. | m | n | Specific Rotatory Power |
|---|---|---|---|---|---|---|---|
| (12)-1 | 7 | 6 | +31.9 | (12)-4 | 10 | 8 | +28.7 |
| (12)-2 | 9 | 6 | +30.0 | (12)-5 | 11 | 6 | +28.3 |
| (12)-3 | 10 | 6 | +29.5 | | | | |

-continued

Compound (13)

| Compound No. | m | n | Specific Rotatory Power | Compound No. | m | n | Specific Rotatory Power |
|---|---|---|---|---|---|---|---|
| (13)-1 | 7 | 6 | +33.0 | (13)-4 | 10 | 8 | +29.3 |
| (13)-2 | 9 | 6 | +31.7 | (13)-5 | 11 | 6 | +30.1 |
| (13)-3 | 10 | 6 | +31.0 | (13)-6 | 11 | 8 | +29.6 |

Compound (14)

| Compound No. | m | n | Specific Rotatory Power | Compound No. | m | n | Specific Rotatory Power |
|---|---|---|---|---|---|---|---|
| (14)-1 | 9 | 6 | +28.6 | (14)-4 | 10 | 8 | +27.8 |
| (14)-2 | 9 | 8 | +28.6 | (14)-5 | 11 | 6 | +27.8 |
| (14)-3 | 10 | 6 | +28.2 | (14)-6 | 11 | 8 | +27.2 |

Compound (15)

| Compound No. | m | n | Specific Rotatory Power |
|---|---|---|---|
| (15)-1 | 11 | 8 | +26.8 |

Compound (16)

| Compound No. | m | n | Specific Rotatory Power |
|---|---|---|---|
| (16)-1 | 10 | 6 | +36.8 |

Compound (17)

| Compound No. | m | n | Specific Rotatory Power |
|---|---|---|---|
| (17)-1 | 6 | 4 | +26.1 |
| (17)-2 | 6 | 5 | +29.9 |
| (17)-3 | 10 | 5 | +27.5 |

Compound (18)

| Compound No. | m | n | X | Specific Rotatory Power | Compound No. | m | n | X | Specific Rotatory Power |
|---|---|---|---|---|---|---|---|---|---|
| (18)-1 | 8 | 6 | H | +30.2 | (18)-5 | 9 | 5 | F | +26.5 |
| (18)-2 | 9 | 6 | H | +29.7 | (18)-6 | 9 | 6 | F | +26.4 |

-continued

| | | | | | | | | |
|---|---|---|---|---|---|---|---|---|
| (18)-3 | 10 | 6 | H | +29.5 | (18)-7 | 10 | 4 | F | +23.4 |
| (18)-4 | 8 | 6 | F | +27.8 | (18)-8 | 10 | 6 | F | +25.2 |

Compound (19)

| Compound No. | m | n | X | Specific Rotatory Power | Compound No. | m | n | X | Specific Rotatory Power |
|---|---|---|---|---|---|---|---|---|---|
| (19)-1 | 8 | 6 | H | +26.4 | (19)-5 | 9 | 5 | F | +23.4 |
| (19)-2 | 9 | 6 | H | +26.4 | (19)-6 | 10 | 4 | F | +21.9 |
| (19)-3 | 10 | 6 | H | +25.9 | (19)-7 | 10 | 6 | F | +26.6 |
| (19)-4 | 8 | 6 | F | +26.6 | | | | | |

Compound (20)

| Compound No. | m | n | X | Specific Rotatory Power | Compound No. | m | n | X | Specific Rotatory Power |
|---|---|---|---|---|---|---|---|---|---|
| (20)-1 | 9 | 4 | H | +30.2 | (20)-5 | 9 | 6 | F | +27.5 |
| (20)-2 | 10 | 5 | H | +27.2 | (20)-6 | 10 | 4 | F | +25.3 |
| (20)-3 | 9 | 4 | F | +25.8 | (20)-7 | 10 | 6 | F | +26.2 |
| (20)-4 | 9 | 5 | F | +27.7 | | | | | |

Compound (21)

| Compound No. | m | n | X | Specific Rotatory Power | Compound No. | m | n | X | Specific Rotatory Power |
|---|---|---|---|---|---|---|---|---|---|
| (21)-1 | 6 | 6 | H | −23.9 | (21)-6 | 10 | 3 | H | −16.1 |
| (21)-2 | 7 | 6 | H | −21.0 | (21)-7 | 10 | 4 | H | −17.9 |
| (21)-3 | 8 | 6 | H | −22.6 | (21)-8 | 8 | 6 | F | −20.7 |
| (21)-4 | 9 | 4 | H | −19.3 | (21)-9 | 10 | 3 | F | −15.5 |
| (21)-5 | 9 | 6 | H | −21.0 | | | | | |

Compound (22)

| Compound No. | m | n | Specific Rotatory Power | Compound No. | m | n | Specific Rotatory Power |
|---|---|---|---|---|---|---|---|
| (22)-1 | 6 | 6 | −21.9 | (22)-3 | 11 | 6 | −14.5 |
| (22)-2 | 7 | 6 | −20.8 | (22)-4 | 12 | 6 | −11.6 |

Compound (23)

| Compound No. | m | n | Specific Rotatory Power | Compound No. | m | n | Specific Rotatory Power |
|---|---|---|---|---|---|---|---|
| (23)-1 | 5 | 6 | −23.1 | (23)-4 | 7 | 4 | −18.5 |

-continued

| | | | | | | | |
|---|---|---|---|---|---|---|---|
| (23)-2 | 6 | 4 | −20.6 | (23)-5 | 7 | 6 | −21.4 |
| (23)-3 | 6 | 6 | −22.4 | (23)-6 | 8 | 6 | −21.9 |

Compound (24)

| Compound No. | m | n | Specific Rotatory Power | Compound No. | m | n | Specific Rotatory Power |
|---|---|---|---|---|---|---|---|
| (24)-1 | 5 | 6 | −20.4 | (24)-3 | 7 | 6 | −19.5 |
| (25)-2 | 5 | 6 | −20.1 | (24)-4 | 9 | 6 | −19.3 |

Compound (25)

| Compound No. | m | n | X | Specific Rotatory Power | Compound No. | m | n | X | Specific Rotatory Power |
|---|---|---|---|---|---|---|---|---|---|
| (25)-1 | 7 | 5 | F | −18.9 | (25)-6 | 9 | 6 | F | −18.9 |
| (25)-2 | 7 | 6 | F | −20.1 | (25)-7 | 10 | 6 | F | −18.8 |
| (25)-3 | 8 | 5 | F | −18.9 | (25)-8 | 11 | 6 | F | −18.1 |
| (25)-4 | 8 | 6 | F | −20.6 | (25)-9 | 10 | 6 | H | −21.6 |
| (25)-5 | 9 | 5 | F | −18.9 | | | | | |

Compound (26)

| Compound No. | m | n | X | Specific Rotatory Power | Compound No. | m | n | X | Specific Rotatory Power |
|---|---|---|---|---|---|---|---|---|---|
| (26)-1 | 6 | 6 | H | −23.5 | (26)-3 | 10 | 6 | H | −22.8 |
| (26)-2 | 10 | 4 | H | −18.6 | (26)-4 | 10 | 6 | F | −19.1 |

Compound (27)

| Compound No. | m | n | X | Specific Rotatory Power | Compound No. | m | n | X | Specific Rotatory Power |
|---|---|---|---|---|---|---|---|---|---|
| (27)-1 | 7 | 6 | H | −27.7 | (27)-5 | 6 | 6 | F | −18.5 |
| (27)-2 | 8 | 6 | H | −22.9 | (27)-6 | 10 | 4 | F | −17.1 |
| (27)-3 | 10 | 4 | H | −18.7 | (27)-7 | 10 | 6 | H | −19.2 |
| (27)-4 | 10 | 6 | H | −21.2 | | | | | |

Compound (28)

| Compound No. | m | n | Specific Rotatory Power | Compound No. | m | n | Specific Rotatory Power |
|---|---|---|---|---|---|---|---|
| (28)-1 | 8 | 5 | −27.8 | (28)-4 | 9 | 5 | −27.4 |
| (28)-2 | 8 | 6 | −27.2 | (28)-5 | 10 | 4 | −24.5 |
| (28)-3 | 9 | 4 | −25.3 | (28)-6 | 10 | 5 | −27.3 |

-continued

Compound (29)

| Compound No. | m | n | Specific Rotatory Power |
|---|---|---|---|
| (29)-1 | 6 | 4 | −20.2 |
| (29)-2 | 6 | 5 | −20.7 |

Compound (30)

| Compound No. | m | n | X | Specific Rotatory Power |
|---|---|---|---|---|
| (30)-1 | 10 | 5 | — | −32.1 |
| (30)-2 | 10 | 5 | COO | −22.9 |

Compound (31)

| Compound No. | m | n | Specific Rotatory Power |
|---|---|---|---|
| (31)-1 | 10 | 3 | −13.8 |

Concrete examples of the composition of the present invention can be obtained by mixing at least one selected from the above compounds (a) and at least one selected from the above compounds (b). However, the present invention is not limited to the compositions of the above compounds.

Figure 3:
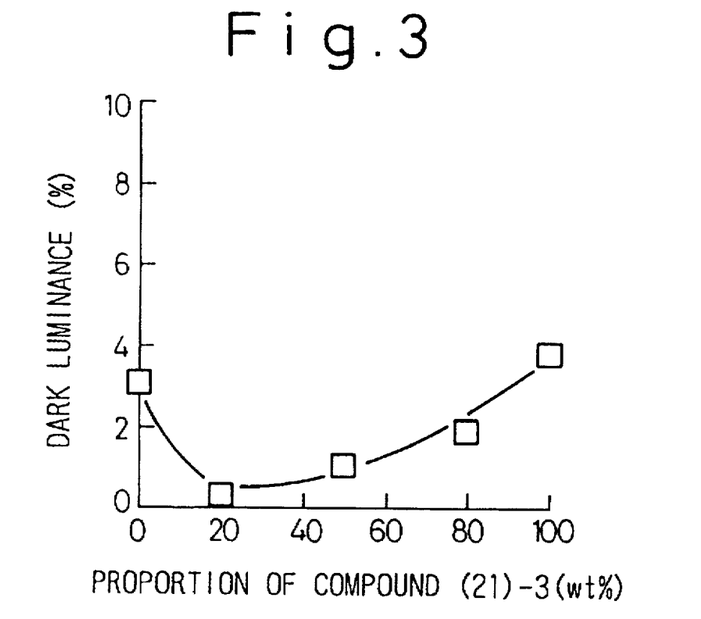
FIG. 3 is a graph showing the relation between the composition of a two component mixture consisting of the compound (1)-7 having a positive specific rotatory power and the compound (21)-3, and the magnitude of the dark luminance.
Figure 4:
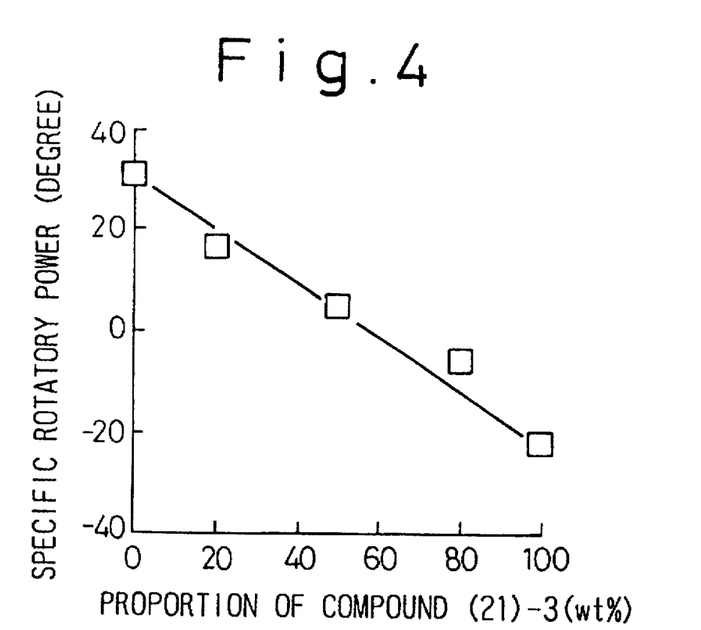
FIG. 4 is a graph showing the composition of the two component mixture of FIG. 3 and its specific rotatory power.

As an example, the magnitude of dark luminance and specific rotatory power of a two component system of the compound (1)-7 included in the group (a)

and the compound (21)-3 included in the group (b)

is shown in FIGS. 3 and 4. FIG. 3 is a diagram of plotted values (%) of dark luminance at a temperature 5° C. lower than the SmC$_A$* phase upper limit temperature of the composition system, and FIG. 4 is a diagram of specific rotatory power.

From FIGS. 3 and 4, it is apparent that the dark luminance of the two component mixture decreases synergistically, and takes the smallest specific rotatory power of 0° and +25°. Both of the two compounds are (R) enantiomers of the absolute configuration. In the case where a two component mixture system is comprised of two compounds of the absolute configuration of the (S) enantiomer, it is apparent from theory that the dark luminance takes the smallest value in the range of 0° to −25° of specific rotatory power.

Figure 5:
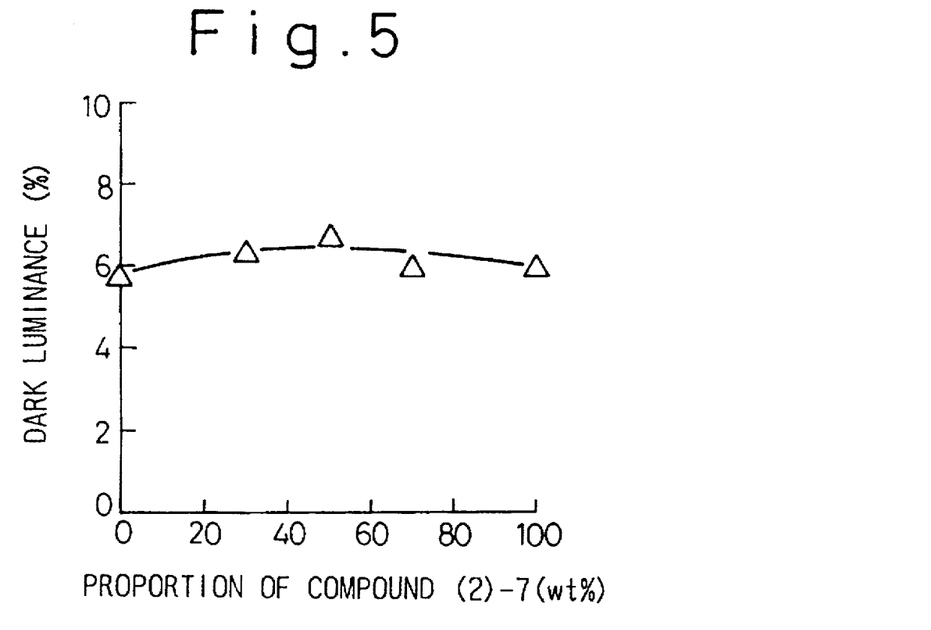
FIG. 5 is a graph showing the relation between the composition of a two component mixture of two compounds having positive specific rotatory powers (the compound (1)-7 and the compound (2)-7), and the magnitude of the dark luminance.
Figure 6:
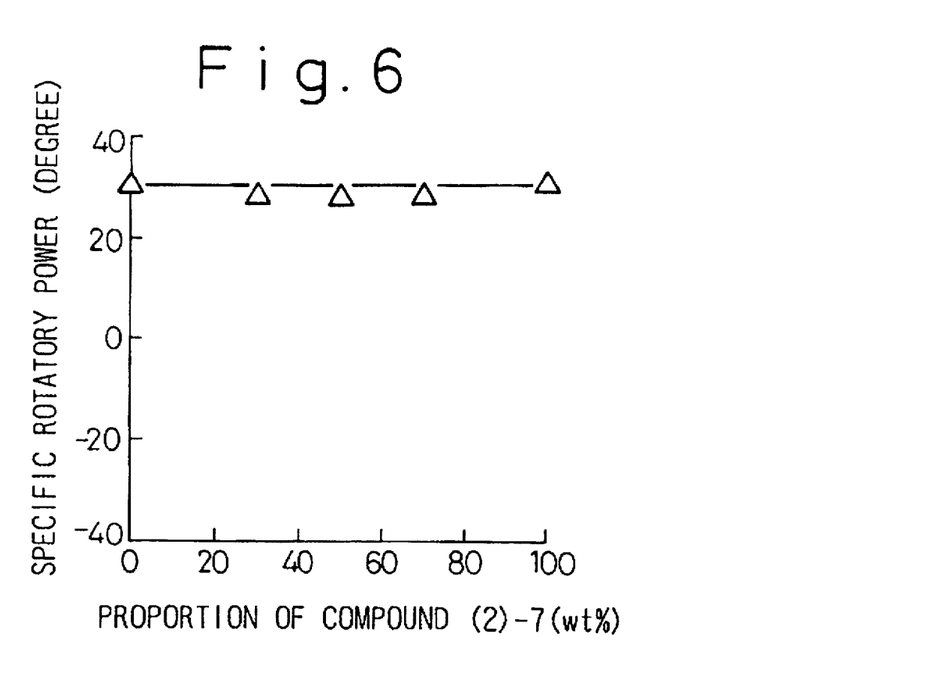
FIG. 6 is a graph showing the composition of the two component mixture of FIG. 5 and the specific rotatory power.
Figure 7:
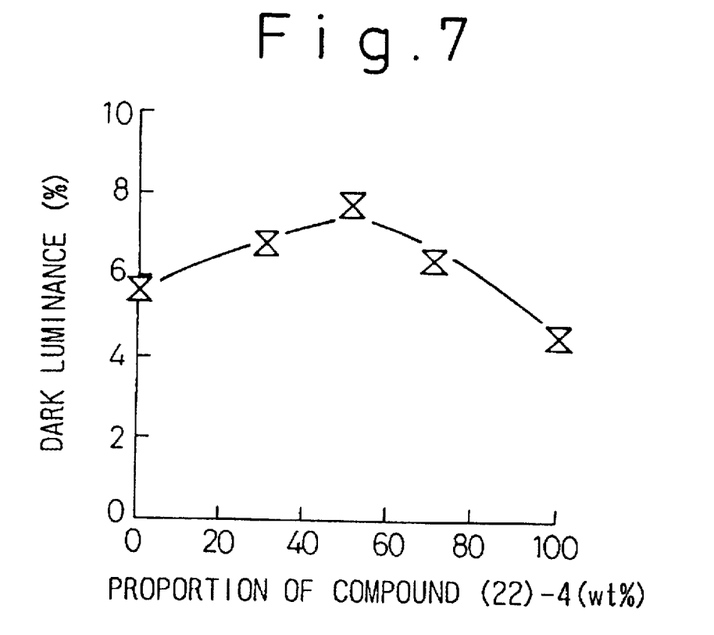
FIG. 7 is a graph showing the relation between the composition of a two component mixture of two compounds having negative specific rotatory powers (the compound (21)-3 and the compound (22)-4), and the magnitude of the dark luminance.
Figure 8:
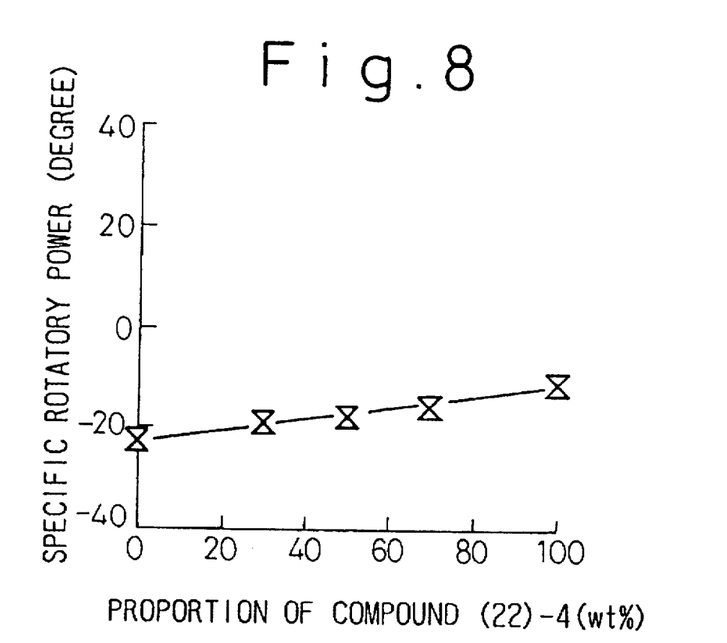
FIG. 8 is a graph showing the composition of the two component mixture of FIG. 7 and its specific rotatory power.

As a comparison, the magnitude of the dark luminance of the two compounds (1)-7 and (2)-7 both included in the group (a) having specific rotatory power of positive values is shown in FIG. 5, and the specific rotatory power thereof is shown in FIG. 6. Further, the magnitude of the dark luminance of the two compounds (21)-3 and (22)-4 both included in the group (b) having specific rotatory power of positive values is shown in FIG. 7, and the specific rotatory power thereof is shown in FIG. 8. From these figures, it is apparent that the mixing of compounds having the same sign of the rotatory power does not decrease the dark luminance.

The present inventors have found that the antiferroelectric liquid crystal composition obtained by mixing chiralsmectic liquid crystal compound(s) having positive specific rotatory power and chiralsmectic liquid crystal compound(s) having negative specific rotatory power shows a synergistic decreases in its dark luminance, and that the dark luminance decreasing effect is maximized in the specific rotatory power range of −25° to +25°.

The following examples are shown in order to illustrate the present invention. However, the examples do not limit the present invention.

The dark luminance, bright luminance and contrast were determined as follows at a temperature 5° C. lower than the maximum temperature of the SmC$_A$* phase, based on the definition described above concerning FIG. 1. First, a polarizing microscope with a photomultiplier light source was adjusted to always exhibit a specific light transmitting intensity, and the light transmitting intensity at that time was set as 100%, and 0% for a completely shaded state. Next, an antiferroelectric liquid crystal display element was put on the polarizing microscope, and a chopping wave voltage was applied on the element under the crossed Nicols, thereafter, the transmitted light intensity was determined at the light-shaded position, with no-electric field applied, and the determined value was transformed into a percentage, which figure was determined as the dark luminance. The antiferroelectric liquid crystal element was obtained by injecting an antiferroelectric liquid crystal material into a cell having a cell gap of 2 μm and obtained by putting spacers between, and sticking together, two sheets of glass substrate which have been provided with electrodes and provided with rubbing treated polyimide alignment film on its surface. The bright luminance was determined by applying a direct voltage to make the cell exhibit a bright state. The contrast was obtained as (bright luminance)/(dark luminance).

The specific rotatory power was determined by dissolving a liquid crystal material in a chloroform solution and using an azimuthal polarimeter at 25° C., with a low pressure sodium lamp (wavelength 586 nm) and an optical path length of 10 cm.

Further, the phase series was determined by observation with a polarizing microscope with a hot stage using the cell.

EXAMPLE 1

Antiferroelectric liquid crystal compositions 1, 2 and 3 having the percentages by weight shown in Table 1 were prepared using the compound (1)-7 of the (a) group and the compound (31)-1 of the (b) group.

TABLE 1

|  | Compound No. | Composit. 1 | Composit. 2 | Composit. 3 |
|---|---|---|---|---|
| Component A | Compd. (1)-7 | 80% | 50% | 20% |
| Component B | Compd. (31)-1 | 20% | 50% | 80% |

The composition 1 showed a $SmC_A^*$ phase in the temperature range of 30° to 105° C., showed a $S_A$ phase at higher temperatures and became an isotropic liquid at 120° C. The composition 2 showed $SmC_A^*$ phase in the temperature range of 40° to 108° C., showed $S_C^*$ and $S_A$ phases at higher temperatures and became an isotropic liquid at 120° C. The composition 3 showed a $SmC_A^*$ phase in the temperature range of 50° to 120° C., showed $S_C^*$ and $S_A$ phases at higher temperatures and became an isotropic liquid at 140° C.

Figure 9:
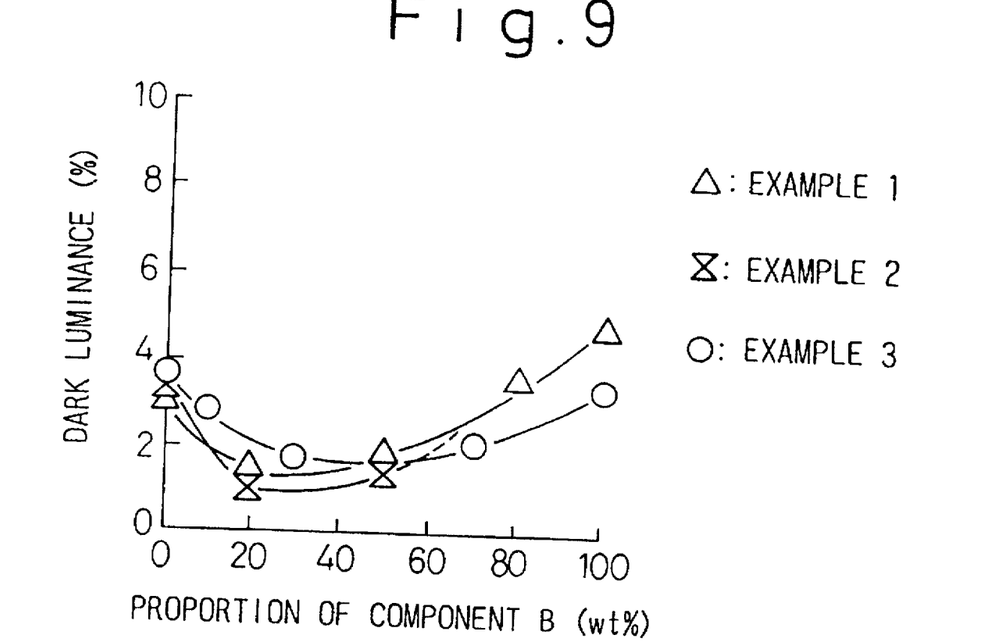
FIG. 9 is a graph showing the relation between the composition of respective two component mixtures consisting of a compound having positive specific rotatory power and a compound having negative specific rotatory powers of Examples 1 to 3.
Figure 10:
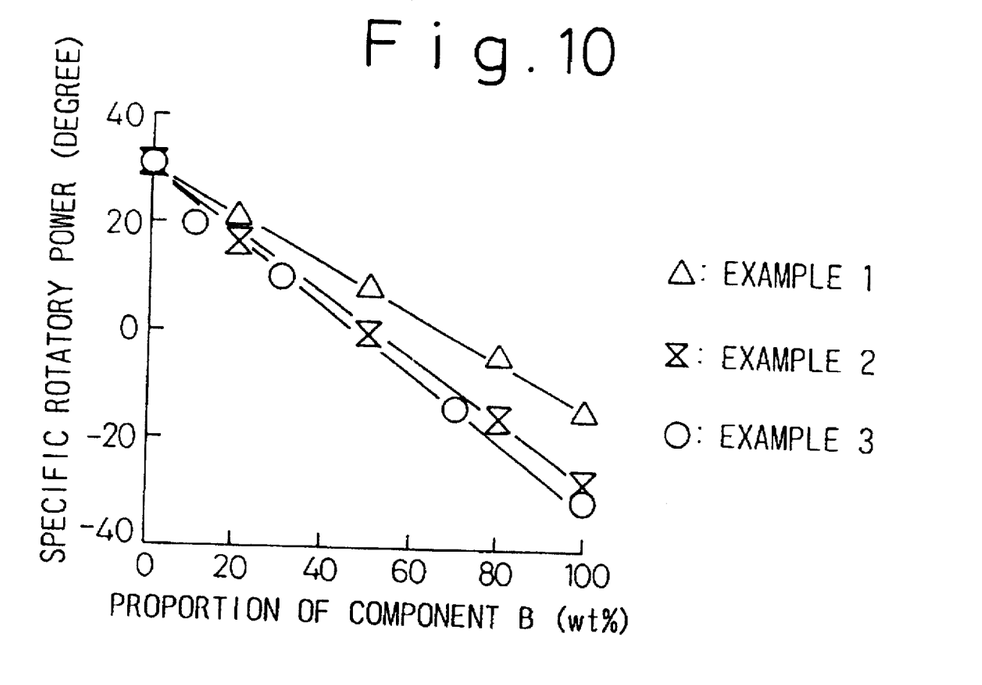
FIG. 10 is a graph showing the composition of the two component mixture of FIG. 9 and the specific rotatory power.

The dark luminance of compounds (1)-7 and (31)-1 and compositions 1 to 3 are shown in FIG. 9 and their specific rotatory powers are shown in FIG. 10. From these figures, it is apparent that the dark luminances exhibits its minimum value in the vicinity of specific rotatory power of +10° to +15°.

The contrast of the composition 1 was 48 (dark luminance: 1.5%, bright luminance: 72%), at 100° C.

EXAMPLE 2

Antiferroelectric liquid crystal compositions 1, 2 and 3 having the percentages by weight shown in Table 2 were prepared using the compound (1)-7 of the (a) group and the compound (28)-1 of the (b) group.

TABLE 2

|  | Compound No. | Composit. 1 | Composit. 2 | Composit. 3 |
|---|---|---|---|---|
| Component A | Compd. (1)-7 | 80% | 50% | 20% |
| Component B | Compd. (28)-2 | 20% | 50% | 80% |

The composition 1 showed a $SmC_A^*$ phase in the temperature range of 40° to 100° C., showed a $S_A$ phase at higher temperatures and became an isotropic liquid at 114° C. The composition 2 showed a $SmC_A^*$ phase in the temperature range of 40° to 80° C., showed $S_C^*$ and $S_A^*$ phases at higher temperatures and became an isotropic liquid at 112° C. The composition 3 did not show a $SmC_A^*$ phase.

The dark luminance of compound (1)-7 and compositions 1 and 2 are shown in FIG. 9 and the specific rotatory powers of the above three and compound 3 and composition (28)-2 are shown in FIG. 10. From these figures, it is apparent that the dark luminance exhibits its minimum value in the vicinity of specific rotatory powers of +10° to +15°.

The contrast of the composition 1 was 48 (dark luminance: 1.5%, bright luminance: 72%), at 100° C.

EXAMPLE 3

Antiferroelectric liquid crystal compositions 1, 2 and 3 having the percentages by weight shown in Table 3 were prepared using the compound (1)-7 of the (a) group and S enantiomers of the compound (1)-7 of the (b) group.

TABLE 3

|  | Compound No. | Composit. 1 | Composit. 2 | Composit. 3 |
|---|---|---|---|---|
| Component A | Compd. (1)-7 | 90% | 70% | 30% |
| Component B | Compd. (1)-7, S | 10% | 30% | 70% |

The composition 1 showed a $SmC_A^*$ phase in the temperature range of 50° to 100° C., showed $S_C^*$ and $S_A$ phases at higher temperatures and became an isotropic liquid at 108° C. The composition 2 showed a $SmC_A^*$ phase in the temperature range of 30° to 76° C., showed $S_C^*$ and $S_A$ phases at higher temperatures and became an isotropic liquid at 108° C. The composition 3 showed a $SmC_A^*$ phase in the temperature range of 30° to 76° C., showed $S_C^*$ and $S_A$ phases at higher temperatures and became an isotropic liquid at 108° C.

The dark luminances of the compound (1)-7, the S enantiomer of the compound (1)-7 and compositions 1 to 3 are shown in FIG. 9 and their specific rotatory powers are shown in FIG. 10. From these figures, it is apparent that the dark luminances exhibit their minimum value in the vicinity of specific rotatory power of 0°.

The contrast of the composition 1 was 42 (dark luminance: 1.8%, bright luminance: 76%), at 71° C.

EXAMPLE 4

Antiferroelectric liquid crystal compositions 1, 2, 3, 4 and 5 having the percentages by weight shown in Table 4 were prepared using six components of the compounds (1)-2, (1)-7, (2)-7 and (2)-9 of the (a) group and the compounds (22)-4 and (28)-2 of the (b) group.

TABLE 4

|  | Compd. No. | Composit. 1 | Composit. 2 | Composit. 3 | Composit. 4 | Composit. 5 |
|---|---|---|---|---|---|---|
| Component A | (1)-2 | 4.7% | 3.5% | 3.0% | 2.5% | 0% |
|  | (1)-7 | 20.3% | 15.0% | 13.0% | 11.0% | 0% |
|  | (2)-7 | 31.3% | 23.1% | 20.0% | 16.9% | 0% |

TABLE 4-continued

|  | Compd. No. | Composit. 1 | Composit. 2 | Composit. 3 | Composit. 4 | Composit. 5 |
|---|---|---|---|---|---|---|
|  | (2)-9 | 43.7% | 32.4% | 28.0% | 23.6% | 0% |
| Component B | (22)-4 | 0% | 11.6% | 16.0% | 20.4% | 44.4% |
|  | (28)-2 | 0% | 14.4% | 20.0% | 25.6% | 55.6% |

The composition 1 showed a SmC$_A$* phase in the temperature range of 0° to 74° C., showed S$_A$ phase at higher temperatures and became an isotropic liquid at 78° C. The composition 2 showed a SmC$_A$* phase in the temperature range of 0° to 70° C., showed S$_C$* and S$_A$ phases at higher temperatures and became an isotropic liquid at 84° C. The composition 3 showed a SmC$_A$* phase in the temperature range of 0° to 65° C., showed S$_C$* and S$_A$ phases at higher temperatures and became an isotropic liquid at 90° C. The composition 4 showed a SmC$_A$* phase in the temperature range of 0° to 68° C., showed S$_C$* and S$_A$ phases at higher temperatures and became an isotropic liquid at 94° C. The composition 5 showed a SmC$_A$* phase in the temperature range of 0° to 74° C., showed a S$_A$ phase at higher temperatures and became an isotropic liquid at 96° C.

Figure 11:
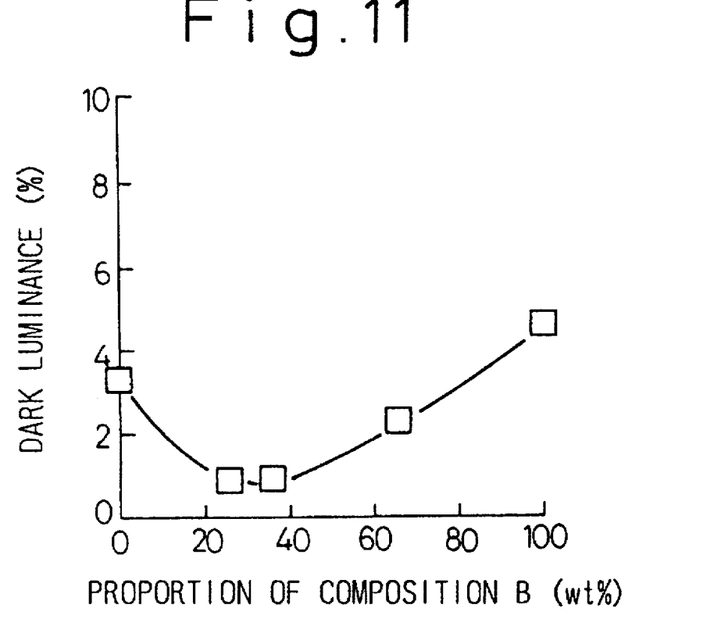
FIG. 11 is a graph showing the relation between the proportion of each group in a mixture of two groups consisting of a group of compounds (composition A) having positive specific rotatory powers and a group of compounds (composition B) having negative specific rotatory powers, and the magnitude of the dark luminance.
Figure 12:
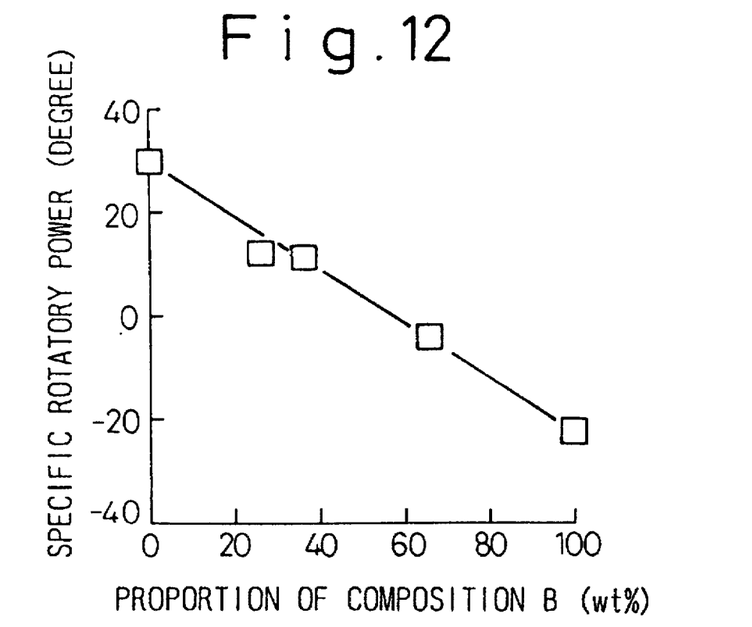
FIG. 12 is a graph showing the proportion of the two groups of FIG. 11 and the specific rotatory power.

The dark luminances of compositions 1 to 5 are shown in FIG. 11 and their specific rotatory powers are shown in FIG. 12. From these figures, it is apparent that the dark luminances exhibit their minimum value in the vicinity of specific rotatory power of +10° to +15°.

The contrast of the composition 3 was 75 (dark luminance: 0.9%, bright luminance: 68%), at 60° C.

As illustrated by the Examples, through mixing compound(s) exhibiting positive specific rotatory power and compound(s) exhibiting negative specific rotatory power, and controlling the specific rotatory power of the composition, antiferroelectric liquid crystal compositions exhibiting lowered dark luminance can be obtained. Further, by using an antiferroelectric liquid crystal composition, antiferroelectric liquid crystal display elements having high contrasts can be obtained.

We claim:

1. An antiferroelectric liquid crystal composition comprising:

at least one first chiralsmectic liquid crystal compound having a positive specific rotatory power $[\alpha]_D^{25}$ (hereinafter the specific rotatory powers described are $[\alpha]_D^{25}$) and an R type absolute configuration; and at least one second chiralsmectic liquid crystal compound having a negative specific rotatory power and an R type absolute configuration, wherein the at least one first and second chiralsmectic liquid crystal compounds are optically active compounds represented by the following general formula (II), wherein m is an integer of 1 to 18; n is an integer of 3 to 10; A, B and C are one or a combination of two selected from the following formulae (III); X$^1$, X$^2$ and X$^3$ are independently selected from the following formulae (IV); Z$^1$, Z$^2$ and Z$^3$ are independently selected from the following formulae (V); and Y is any one of CH$_3$, CF$_3$, C$_2$H$_5$ and C$_2$F$_5$, (III):

(IV) single bond (—), —COO—, —OCO—, —CO—, —O—, —CH$_2$O— and —C≡C—, and (V) H, F, Cl, Br, CN and CH$_3$, and wherein the composition has a specific rotatory power of from 0° to +25°.

2. The antiferroelectric liquid crystal composition according to claim 1, wherein Y in the at least one first chiralsmectic liquid crystal compound is CF$_3$, and wherein Y in the at least one second chiralsmectic liquid crystal compound is CH$_3$.

3. The antiferroelectric liquid crystal composition according to claim 1, which comprises 40 to 90% by weight of the at least one first chiralsmectic liquid crystal compound represented by the formula (II) wherein the absolute configuration is R type and the specific rotatory power is positive, and 10 to 60% by weight of the at least one second chiralsmectic liquid crystal compound represented by the formula (II) wherein the absolute configuration is R type and the specific rotatory power is negative.

4. A liquid crystal display device comprising the liquid crystal composition according to claim 1.

5. A liquid crystal display device comprising the liquid crystal composition according to claim 2.

6. A liquid crystal display device comprising the liquid crystal composition according to claim 3.

7. An antiferroelectric liquid crystal composition comprising:

at least one first chiralsmectic liquid crystal compound having a negative specific rotatory power and an S type absolute configuration; and at least one second chiralsmectic liquid crystal compound having a positive specific rotatory power and an S type absolute configuration, wherein the at least one first and second chiralsmectic liquid crystal compounds are optically active compounds represented by the following general formula (II), wherein m is an integer of 1 to 18; n is an integer of 3 to 10; A, B and C are one or a combination of two selected from the following formulae (III); $X^1$, $X^2$ and $X^3$ are independently selected from the following formulae (IV); $Z^1$, $Z^2$ and $Z^3$ are independently selected from the following formulae (V); and Y is any one of $CH_3$, $CF_3$, $C_2H_5$ and $C_2F_5$.

(III):

(IV) single bond (—), —COO—, —OCO—, —CO—, —O—, —CH$_2$O— and —C≡C—, and (V) H, F, Cl, Br, CN and $CH_3$, and wherein the composition has a specific rotatory power of from −25° to 0°.

8. The antiferroelectric liquid crystal composition according to claim 7, wherein Y in the at least one first chiralsmectic liquid crystal compound is $CF_3$, and wherein Y in the at least one second chiralsmectic liquid crystal compound is $CH_3$.

9. The antiferroelectric liquid crystal composition according to claim 7, which comprises 40 to 90% by weight of the at least one first chiralsmectic liquid crystal compound represented by the formula (II) wherein the absolute configuration is S type and the specific rotatory power is negative, and 10 to 60% by weight of the at least one second chiralsmectic liquid crystal compound represented by the formula (II) wherein the absolute configuration is S type and the specific rotatory power is positive.

10. A liquid crystal display device comprising the liquid crystal composition according to claim 7.

11. A liquid crystal display device comprising the liquid crystal composition according to claim 8.

12. A liquid crystal display device comprising the liquid crystal composition according to claim 9.

13. An antiferroelectric liquid crystal composition comprising:

at least one first chiralsmectic liquid crystal compound having a positive specific rotatory power and an asymmetric chemical constitution; and at least one second chiralsmectic liquid crystal compound having a negative specific rotatory power and an asymmetric chemical constitution, wherein the at least one first and second chiralsmectic liquid crystal compounds are represented by the following formula (I), wherein R is any one of $CH_3$, $CF_3$, $C_2H_5$ and $C_2F_5$, and wherein an absolute configuration of the at least one first and second chiralsmectic liquid crystal compounds are both R type or both S type, and the composition has a specific rotatory power of from −25° to +25°.

14. A liquid crystal display device comprising the liquid crystal composition according to claim 13.

* * * * *